United States Patent
Kim et al.

(10) Patent No.: US 8,261,611 B2
(45) Date of Patent: Sep. 11, 2012

(54) METHOD FOR ANALYZING GAIT PATTERN

(75) Inventors: Min Ho Kim, Daejeon (KR); Ho Youl Jung, Daejeon (KR); Jae Won Jang, Daejeon (KR); Sa Kwang Song, Daejeon (KR); Soo Jun Park, Seoul (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 84 days.

(21) Appl. No.: 12/969,565

(22) Filed: Dec. 15, 2010

(65) Prior Publication Data

US 2011/0146396 A1   Jun. 23, 2011

(30) Foreign Application Priority Data

Dec. 22, 2009 (KR) .................. 10-2009-0129206

(51) Int. Cl.
*A61B 5/103*   (2006.01)
(52) U.S. Cl. ..................... 73/172; 600/592
(58) Field of Classification Search .............. 73/172; 600/592
See application file for complete search history.

(56) References Cited

U.S. PATENT DOCUMENTS

| | | | | |
|---|---|---|---|---|
| 5,566,479 A | * | 10/1996 | Gray et al. | 36/137 |
| 6,195,921 B1 | | 3/2001 | Truong | |
| 6,836,744 B1 | | 12/2004 | Asphahani et al. | |
| 7,204,041 B1 | * | 4/2007 | Bailey et al. | 36/29 |
| 7,219,449 B1 | * | 5/2007 | Hoffberg et al. | 36/88 |
| 2011/0054358 A1 | * | 3/2011 | Kim et al. | 600/592 |
| 2011/0054359 A1 | * | 3/2011 | Sazonov et al. | 600/595 |

FOREIGN PATENT DOCUMENTS

| | | |
|---|---|---|
| JP | 10-228540 A | 8/1998 |
| KR | 10-2007-0071308 A | 7/2007 |
| KR | 10-2007-0100592 A | 10/2007 |
| KR | 10-2008-0102466 A | 11/2008 |

* cited by examiner

*Primary Examiner* — Andre Allen

(57) ABSTRACT

A method for analyzing a gait pattern includes: measuring, by a plurality of force sensing resistor (FSR) sensors, foot pressure values, and outputting the measured foot pressure values, respectively; searching for a maximum pressure local area in which the sum of the output values from the FSR sensors included in each of a plurality of pressure local areas is maximized; calculating a center of pressure (COP) with respect to the detected maximum pressure local area; and analyzing a gait pattern by adding the calculated COP to the trajectory of COPs.

5 Claims, 3 Drawing Sheets

METHOD FOR ANALYZING GAIT PATTERN

CROSS-REFERENCE TO RELATED APPLICATIONS

This application claims the priority of Korean Patent Application No. 10-2009-0129206 filed on Dec. 22, 2009, in the Korean Intellectual Property Office, the disclosure of which is incorporated herein by reference.

BACKGROUND OF THE INVENTION

1. Field of the Invention

The present invention relates to a method for analyzing a gait pattern and, more particularly, to a gait pattern analyzing method for calculating a center of pressure (COP) by using a local area having a maximum force sensing resistor (FSR) sum by reflecting (or considering) the characteristics of an insole type FSR sensor and the characteristics of the skeletal structure of a foot.

2. Description of the Related Art

In "Movement, Posture, and Gait Measuring Method and Treatment System" (Korean Patent Registration No. 10-0894895), a center of gravity (COG) and a center of pressure (COP) are calculated by using signals from FSR sensors in relation to gait measurement. In this case, a plurality of FSR sensors are used, and a maximum FSR output value is detected from among the values measured by using the plurality of FSR sensors, which is estimated as the COP.

However, the algorithm estimating the maximum FSR output value as the COP is problematic when applied to a general FSR sensor manufactured in the shape of a shoe insole. Namely, the FSR sensor generates a high value when the pressure is applied to an accurate point due to its characteristics; however, when the skeletal structure of a foot is taken into consideration, an FSR sensor to which a maximum pressure is not applied may have a higher value in actuality. For example, if the FSR sensor is exactly placed at the bottom of the bone of the toe, even when the strongest pressure is applied to the bottom of the front portion of a first metatarsus in actuality, an FSR sensor of the corresponding toe may have the highest FSR output value.

Thus, in the related art, the COP calculation is inaccurately performed due to the failure of properly reflecting (or considering) the skeletal structure of a foot and the characteristics of the FSR sensors. Also, when the COP is calculated by simply averaging the entire FSR pressure values, an unnecessary pressure value generated as a user wears shoes is reflected (or included) in the COP calculation.

SUMMARY OF THE INVENTION

An aspect of the present invention provides a gait pattern analyzing method for calculating a center of pressure (COP) by using a local area having a maximum force sensing resistor (FSR) sum by reflecting (or considering) the characteristics of an insole type FSR sensor and the characteristics of a skeletal structure of a foot.

According to an aspect of the present invention, there is provided a method for analyzing a gait pattern including: measuring, by a plurality of force sensing resistor (FSR) sensors, foot pressure values, and outputting the measured foot pressure values, respectively; searching for a maximum pressure local area at which the sum of the output values from the FSR sensors included in each of a plurality of pressure local areas is maximized; calculating a center of pressure (COP) with respect to the detected maximum pressure local area; and analyzing a gait pattern by adding the calculated COP to the trajectory of COPs.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
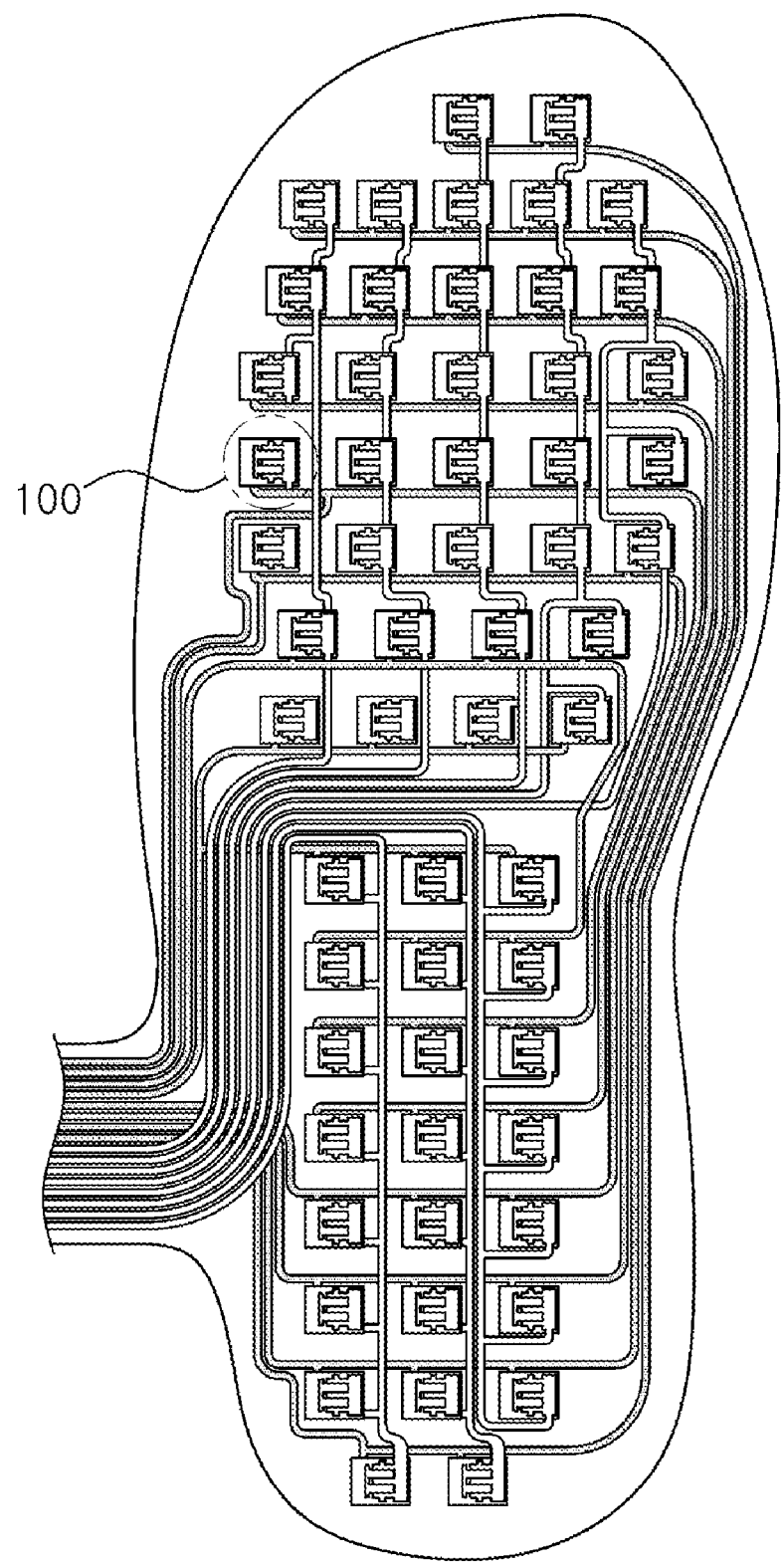
FIG. 1 is a plan view showing the structure of insole type FSR sensors according to an exemplary embodiment of the present invention.

Exemplary embodiments of the present invention will now be described in detail with reference to the accompanying drawings. The invention may however be embodied in many different forms and should not be construed as limited to the embodiments set forth herein. Rather, these embodiments are provided so that this disclosure will be thorough and complete, and will fully convey the scope of the invention to those skilled in the art. In the drawings, the shapes and dimensions may be exaggerated for clarity, and the same reference numerals will be used throughout to designate the same or like components.

FIG. 1 is a plan view showing the structure of insole type FSR sensors according to an exemplary embodiment of the present invention.

As shown in FIG. 1, in the present exemplary embodiment, 58 FSR sensors 100 are used to analyze a gait pattern. However, more FSR sensors or less FSR sensors may be used than are depicted therein. Also, FSR sensors having a larger or smaller size may be used.

Figure 2:
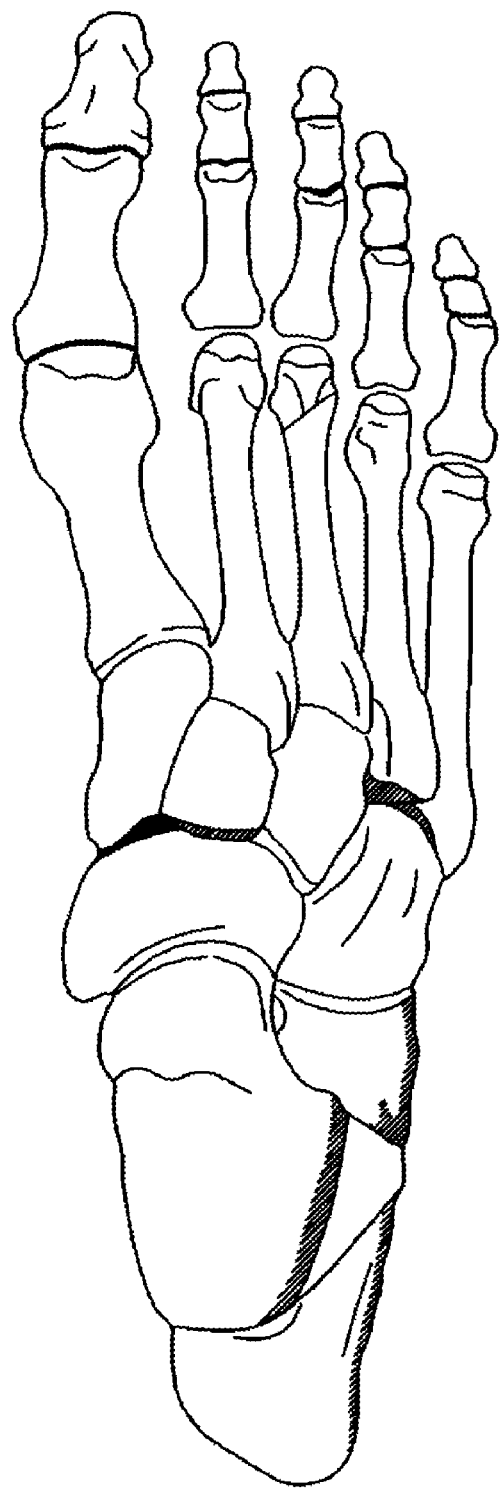
FIG. 2 is a photograph showing a skeletal structure of a foot.

FIG. 2 is a photograph showing a skeletal structure of a foot.

As shown in FIG. 2, portions of the bones of the foot above the sole are protruded. Thus, when the user wears the shoes including the insole type FSR sensors, the protruded portions may directly press the FSR sensors. Thus, even if a larger force is applied to a different portion in actuality, when force is exactly applied to the FSR sensor of the protruded portion, a high FSR output value may be caused even by the smaller force.

Meanwhile, a using a trajectory of the center of pressures (COPs) is one of general methods for analyzing gait. The calculation of the COP trajectory is made while the foot is in contact with the ground. In detail, the calculation of the COP trajectory is made starting from a heel strike (HS) in which the foot is first brought into contact with the ground to a toe-off (TO) in which the toe is separated from the ground.

The HS and the TO may be detected by using a change in the pressure value detected by the FSR sensors. The method of detecting the HS and the TO is out of the technical coverage of the present invention and a known art, so a detailed description thereof will be omitted.

Figure 3:
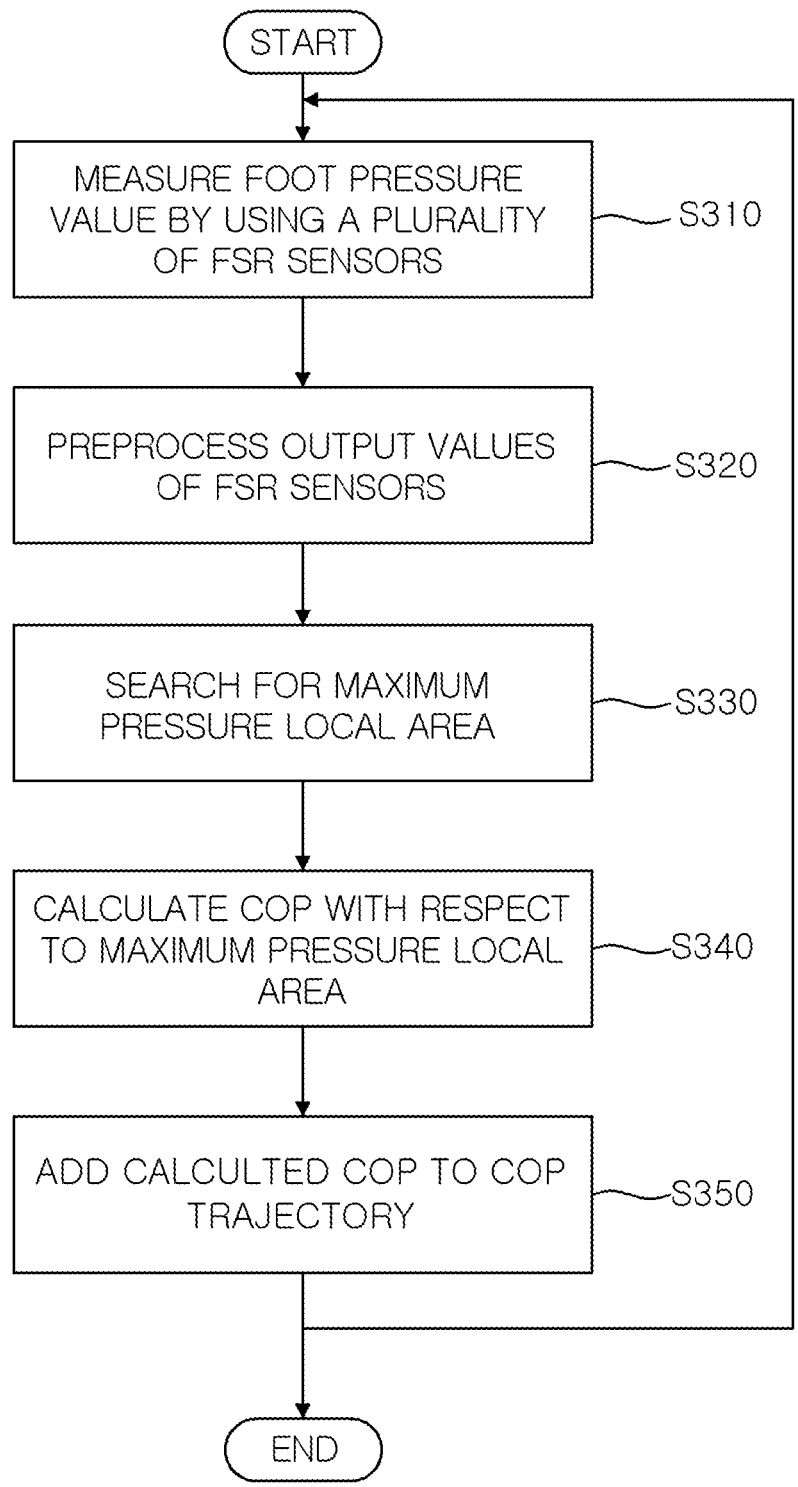
FIG. 3 is a flow chart illustrating the process of a method for analyzing a gait pattern according to an exemplary embodiment of the present invention.

FIG. 3 is a flow chart illustrating the process of a method for analyzing a gait pattern according to an exemplary embodiment of the present invention.

In the present exemplary embodiment, the COP trajectory from the point in time the heel comes into contact with the ground and to the point in time the toe is separated from the ground is calculated. When the heel's contact with the ground is detected, calculation is performed in a state of an initialized COP trajectory.

With reference to FIG. 3, a foot pressure value is measured by using the plurality of FSR sensors 100 (step S310). In this case, output values from the FSR sensors 100 are values obtained by sampling foot input values by more than a total number of rows of left and right FSR sensors (e.g., two lines when one side has L line). For example, when the left and right FSR sensors have a total of 15 rows, fifteen or more times of sampling per second is performed on the foot input value.

Subsequently, the output values of the FSR sensors 100 are preprocessed (step S320). In this preprocessing, an output values of the FSR sensors 100 which is lower than a pre-set reference value is initialized to be 0. Also, an island, namely, an error, of the FSR sensors 100 is removed. Here, the island refers to an FSR sensor which solely has a high output value while the other neighboring FSR sensors have a low output values. This problem is caused as the FSR sensor wrinkles.

After the preprocessing, a maximum pressure local area, at which the sum of the output values of the FSR sensors included in each of the plurality of pressure local areas is maximized, is searched (step S330). Here, the pressure local area refers to an aggregate of the FSR sensors 100 connected to each other, and in this case, 'connected' refers to the relationship of the corresponding FSR sensors when neighboring FSR sensors have output values higher than the pre-set reference value.

The method of detecting the maximum pressure local area among the plurality of pressure local areas in step S330 will now be described.

The sum of output values of the FSR sensors 100 included in each of the pressure local areas is obtained. The sum of the output values is the pressure, which has been applied to the foot, distributed to the FSR sensors 100. The sum of the output values has a value proportional to the actually applied force.

Thus, the sum of the output values is determined as a total pressure value (($F_{total}$ (i), a total pressure value of the ith pressure local area).

Subsequently, an area having the maximum ($F_{total}$ (i) value, among the plurality of pressure local areas, is determined as a maximum pressure local area.

Finally, a COP, with respect to the detected maximum pressure local area, is calculated (step S340), and the calculated COP is added to the COP trajectory, thereby analyzing a gait pattern (step S350).

As set forth above, in the gait pattern analyzing method according to exemplary embodiments of the invention, a COP trajectory is calculated by reflecting the characteristics of the FSR sensors and the skeletal structure of a foot. Thus, an error in a COP calculation which may be caused due to a failure of properly reflecting or considering the characteristics of the skeletal structure of the foot and the characteristics of the FSR sensors can be solved, and thus, a gait pattern can be accurately analyzed.

While the present invention has been shown and described in connection with the exemplary embodiments, it will be apparent to those skilled in the art that modifications and variations can be made without departing from the spirit and scope of the invention as defined by the appended claims.

What is claimed is:

1. A method for analyzing a gait pattern, the method comprising:
   measuring, by a plurality of force sensing resistor (FSR) sensors, foot pressure values, and outputting the measured foot pressure values, respectively;
   searching for a maximum pressure local area at which the sum of the output values from the FSR sensors included in each of a plurality of pressure local areas is maximized;
   calculating a center of pressure (COP) with respect to the detected maximum pressure local area; and
   analyzing a gait pattern by adding the calculated COP to the trajectory of COPs.

2. The method of claim 1, further comprising:
   removing an island as an error from the output values of the plurality of FSR sensors.

3. The method of claim 2, wherein the output values of the plurality of FSR sensors are values obtained by sampling the foot pressure values by more than the total number of rows of left and right FSR sensors.

4. The method of claim 1, wherein the pressure local areas are an aggregate of the FSR sensors each connected with an output value greater than a pre-set reference value.

5. The method of claim 1, wherein the detecting of the maximum pressure local area comprises:
   calculating the sum of the output values from the FSR sensors included in each of the pressure local areas;
   determining the calculated sum of the output values as a total pressure value representing each of the pressure local area; and
   detecting a pressure local area having a maximum total pressure value among the plurality of pressure local areas, as the maximum pressure local area.

* * * * *